(12) United States Patent
Bergsma et al.

(10) Patent No.: US 6,187,544 B1
(45) Date of Patent: Feb. 13, 2001

(54) METHODS FOR RAPID CLONING FOR FULL LENGTH CDNAS USING A POOLING STRATEGY

(75) Inventors: Derk Jon Bergsma, Berwyn; Jeffrey L Mooney, Limerick, both of PA (US)

(73) Assignee: SmithKline Beecham Corporation, Philadelphia, PA (US)

( * ) Notice: Under 35 U.S.C. 154(b), the term of this patent shall be extended for 0 days.

(21) Appl. No.: 09/423,190

(22) PCT Filed: Jun. 4, 1998

(86) PCT No.: PCT/US98/11671

§ 371 Date: Nov. 3, 1999

§ 102(e) Date: Nov. 3, 1999

(87) PCT Pub. No.: WO98/55502

PCT Pub. Date: Dec. 10, 1998

Related U.S. Application Data

(60) Provisional application No. 60/048,973, filed on Jun. 4, 1997.

(51) Int. Cl.$^7$ .............................. C12Q 1/68; C12P 19/34; C12N 9/00; C07H 21/02; C07H 21/04
(52) U.S. Cl. ............................ 435/6; 435/91.1; 435/91.2; 435/183; 435/283.1; 435/287.1; 536/23.1; 536/23.2; 536/23.5; 536/24.3; 536/24.31; 536/25.32

(58) Field of Search .............................. 435/6, 91.1, 91.2, 435/183, 283.1, 287.1; 536/23.1, 23.2, 23.5, 24.3, 24.31–24.33, 25.32

(56) References Cited

U.S. PATENT DOCUMENTS 5,219,989   6/1993   Sonenberg et al. .................. 530/350

OTHER PUBLICATIONS

Munroe et al PNAS vol. 92 pp. 2209–2213 Mar. 1995.*
Shepard et al. "Preparation and Screening of an arrayed human genomic library generated with PI cloning system" Proc. Natl. Acad. Sci. USA. (Mar. 1994) vol. 91, pp. 2629–2633.

(List continued on next page.)

Primary Examiner—Kenneth R. Horlick
Assistant Examiner—Jeffrey Siew
(74) Attorney, Agent, or Firm—William T. Han; William T. King; Charles M. Kinzig

(57) ABSTRACT

The present invention provides a method for high throughput cloning of full length cDNA sequences using a pooling strategy. This method uses a plurality of clone arrays prepared from cDNA libraries which have been preferably enriched for 5 ' mRNA sequences and size fractionated into several discrete ranges (sub-libraries). These arrays are used to rapidly identify the full length cDNA sequence for a DNA segment of interest.

13 Claims, 2 Drawing Sheets

OTHER PUBLICATIONS

Bentley et al., The Development and Application of Automated Gridding for Efficient Screening of Yeast and Bacterial, Ordered Libraries. Genomics (1992), vol. 12, No. 3, pp. 534–541.

McAlinden et al., "A Practical Method to Screen Libraries of Cloned DNA." Analytical Biochemistry (1994), vol. 218, pp. 237–238.

Yoshida et al., "A simple and efficient method for constructing high resolution physical maps" Nucleic Acids Research (1993), vol. 21, No. 15, pp. 3553–3562.

Zhang et al., "Gene isolation through genomic complementation using an indexed library of Chlamydomonas reinhardtii DNA" Plant Molecular Biology. (1994), vol. 24, pp. 663–672.

Green et al., "Systematic screening of yeast artical–chromesome libraries by use of the polymerase chain reaction", Proc. Natl. Acad. Sci. USA, Feb. 1990, vol. 87, pp. 1213–1217.

Kwiatkowski et al., "Rapid identification of yeast artifical chromosome clones by matrix pooling and crude lysate PCR." Nucleic Acids Research (1990), vol. 18, No. 23, pp. 7191–7192.

* cited by examiner

METHODS FOR RAPID CLONING FOR FULL LENGTH CDNAS USING A POOLING STRATEGY

This application claims benefit to provisional application 60/048,973 filed Jun. 4, 1997.

FIELD OF THE INVENTION

The present invention relates to a simple, rapid, and cost effective method for the identification and isolation of full length cDNA clones. The method also provides a means to isolate two or more separate, full length cDNA clones for each target gene sequence of interest. This method provides an alternative to traditional library screening technologies.

BACKGROUND OF THE INVENTION

Identification, sequencing and characterization of genes is a major goal of modern scientific research. By identifying genes, determining their sequences and characterization of their biological function, it is possible to employ recombinant technology to produce large quantities of valuable gene products, e.g. proteins and peptides. Additionally, knowledge of gene sequences can provide a key to diagnosis, prognosis and treatment in a variety of disease states in plants and animals which are characterized by inappropriate expression and/or repression of selected genes or by the influence of external factors, e.g., carcinogens or teratogens, on gene function.

As thousands of EST (expressed sequence tag) assemblies for potentially therapeutic gene targets are present in both public and private sequence databses. Analysis of assembly databases can provide insight as to which genes should be further studied for potential use as therapeutic targets or agents. However, such studies are limited unless the intact full length sequence is available for use. Advances in DNA sequencing technology and computational methodologies have drastically altered the rate at which sequencing projects and gene identification can proceed. Literally thousands of cDNA clones, or ESTs, can be randomly sequenced weekly and then computationally assembled into distinct genes. As roughly only 10% of the members of a standard, polyA primed cDNA library are full length, these computational assemblies rarely contain the sequence of the entire expressed gene. This necessitates several rounds of library screening in order to identify an intact full length cDNA clone for practically any gene one wishes to study. These screening procedures can often be inefficient, costly, and time consuming.

Accordingly, there exists a need for a more efficient and rapid method of identifying and isolating thousands of full length cDNA clones. This method must be simple, robust, and enable the identification of multiple cDNA clones for the target gene of interest.

SUMMARY OF THE INVENTION

The present invention provides a method for high throughput cloning of full length cDNA sequences. This method uses a plurality of clone arrays prepared from cDNA libraries which have been preferably enriched for 5' mRNA sequences and size fractionated into several discrete ranges (sub-libraries). These arrays are used to rapidly identify the full length cDNA sequence for a DNA segment of interest.

DETAILED DESCRIPTION

Figure 1:
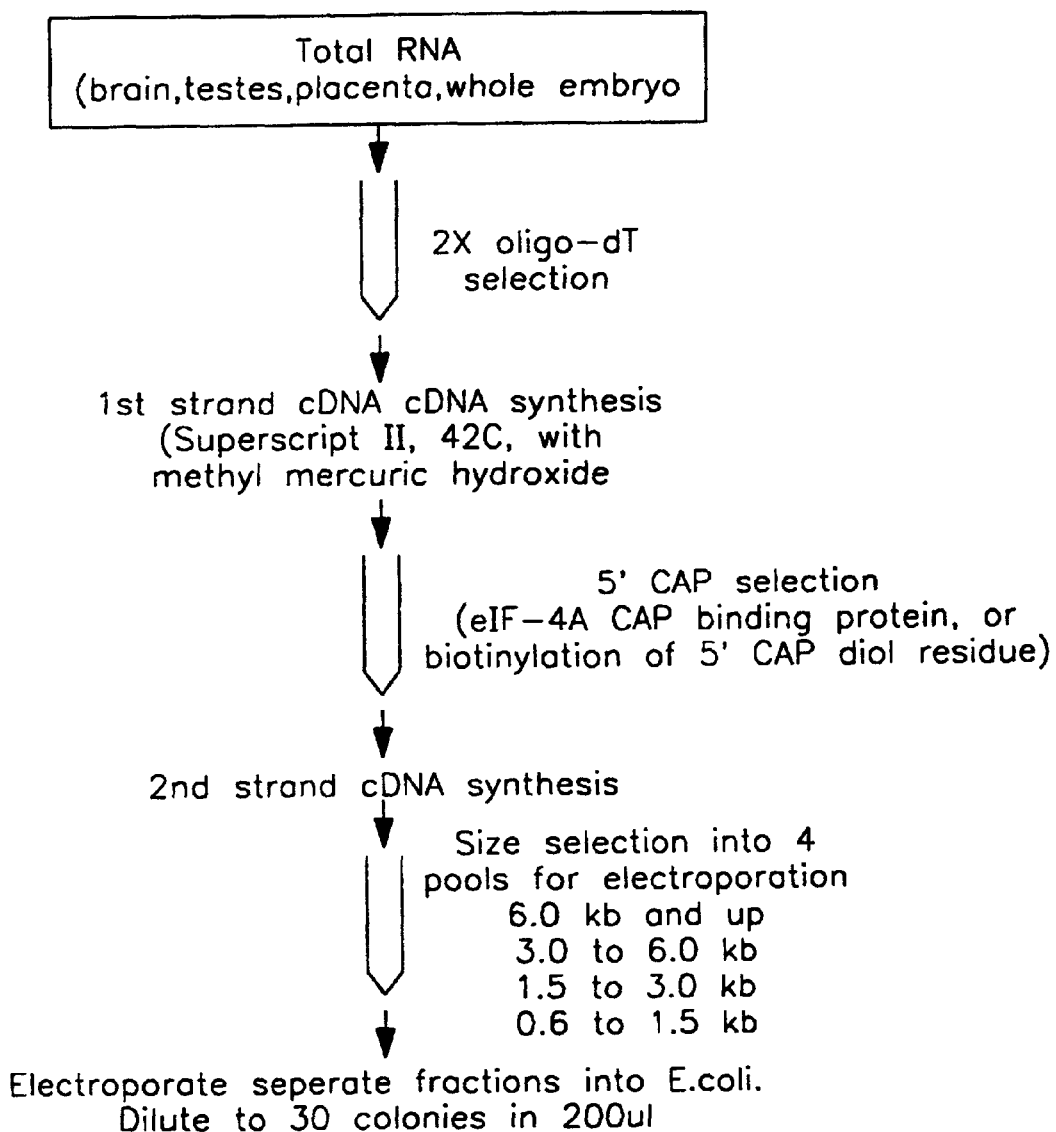
FIG. 1. Schematically describes one example of making size selected cDNA sub-libraries from one tissue source. (Many sets of sub-libraries can be made similarly from diffrent tissue sources for performing the analysis simultaneously.)

In one aspect, the invention provides a method for high throughput full length cDNA cloning of DNA sequences of interest. In one embodiment, the method involves the constructing from a tissue source four cDNA sub-libraries which have different insert sizes; e.g., 1)>6 kb insert size, 2) 3 to 6 kb insert size, 3) 1.5 to 3 kb, and 4) 0.6 to 1.5 kb. Preferably, before size selected cDNA sub-libraries are made, they are pre-enriched for mRNA 5' sequences by a method described below. These size fractionated cDNA clones are then arranged into a 96 well microtiter dish such that 30 clones from a specific insert size pool (sub-library) are placed into each of the wells. A total of 384 microtiter dishes are thus prepared for a total of $1.105 \times 10^6$ clones per four sub-libraries. Following overnight liquid culture growth and the replicating of each microtiter dish, the cells from an individual plate are pooled, and the DNA purified to yield single plate pools of DNA. Aliquots from each of the single plate DNA pools are then arrayed into the wells of a 384 well microtiter dish. The single plate pools are arrayed such that those DNAs derived from the same size fractionation pool are placed into the same quadrant of the 384 well microtiter dish. Equal aliquots from each of the 384 wells are then used to make row and column pools for a total of 40 multi-plate pools for each tissue library (total of four sub-libraries). Each column pool represents the DNA from 24 96 well dishes (69,120 clones) and each row pool represents the DNA from 16 96 well dishes (46,080 clones). The row and column DNA pools for each tissue library are analyzed for for the presence of a specific DNA segment by PCR (polymerase chain reaction). PCR products are separated by gel electrophoresis and detected by ethidium bromide staining to identify the multi-plate row and columnn DNA pools generating the appropriate PCR product. Row and column identification allows for the concomitant identification of both the original insert size fraction pool and the single plate pool yielding the appropriate PCR product. PCR is then performed on row and column pools derived from the positively identified 96 well plates having the largest cDNA insert size. Gel electrophoresis is once again used to determine the row and column pools generating the appropriately sized PCR product and thus identifying the specific well containing the corresponding full length clone. An aliquot of the identified well is then plated with 96 colonies which will undergo PCR analysis. DNA from colonies positive by PCR analysis are then prepared and undergo sequence verification. The above process can done simultaneously by making cDNA libraries from many tissue sources in order to maximize the odds of identifying the desired full-length clone of interest.

As an alternative approach, the arrayed cDNA pools from the 384 well microtiter plate can be arrayed/spotted onto a solid support into predifined positions and then hybridized against labeld DNA probes derived from the partial gene(s) of interest. Positively hybridizing spots would thereby identify the original microtiter plate and eventual clone of interest.

As can be seen from above the essense of the invention lies in: (a) subdividing the cDNA made from a tissue source into different size fractions; and (b) arraying and pooling the clones in such a fashion that allows one to rapidly locate the clones of interest containing the longest insert. Many variations employing this basic approach is possible. Other objects, features, advantages, and aspects of the present invention are apparent to those skilled in the art from the following description. Thus it should be understood that the examples illustrated herein, while indicating a few of the many possible embodiments, are given by way of illustration only. Various changes and modifications within the scope of the invention are readily apparent to those skilled in the art.

Thus in one embodiment, the present invention provides a method for high throughput cloning of full length cDNA sequences, comprising:

(a) preparing cDNAs from mRNAs;

(b) size selecting the cDNAs into discrete n ranges;

(c) transforming host cells with cDNAs from the each discrete n size ranges to make n separate sub-libraries;

(d) placing up to m number of clones from each n sub-libraries into individual wells of k numbers of microtiter plates, each microtiter plates containing x numbers of rows and y numbers of columns, in a fashion that clones from each n sub-library will go into n separate sets of microtiter plates within the total k number of microtiter plates;

(e) pooling all the clones from individual microtiter plates, and placing each pool of clones into wells of a second separate microtiter plate containing i rows and j columns, the second microtiter plate containing a total of k number of wells in such a fashion that placement of pools of clones will be placed in separate n regions within the microtiter plate in order to facilite the identification of cDNA insert sizes;

(f) identifying the well location of cDNA of interest in the second microtiter plate which has the longest insert; and correlating the well located to one of the earlier k number of microtiter plates; and (g) identifying the well location in the microtiter correlated in step (f) for the cDNA of interest;

in which m is a positive integer equal or greater than one; n, k, x, y, i, and j are positive integers greater than one; and with the proviso i times j equals k. Preferably m is 1 to 2000; n, k, x, y, i, and j are 2 to 2000. Even more preferably n is 4, m is 30; k is 384; x is 8; y is 12; i is 16; and j is 24.

The method preferably further comprises the step of enriching the cDNA for full length after step (a) but before step (b). The method of enriching the cDNA preferably comprises treating mRNA/cDNAs duplexes with the single-stranded nuclease, RNase A, and purifying full-length cDNAs via their retained 5° CAP structure by affinity selection using the human cap binding protein, eIF-4E.

Another aspect of the method comprises the step of picking the clone with cDNA of interest if the well identified in step (g) contains more than one clone (i.e. m is greater than 1).

Yet another aspect relates to steps (f) and/or (g) comprising performing PCR reaction with pooled product of rows and columns using primers derived from the cDNA of interest or performing hybridization reaction with cDNA of interest with pools spotted on a solid matrix support.

Thus the above embodiment uses a plurality of clone arrays prepared from cDNA libraries which have been preferably enriched for 5' mRNA sequences and size fractionated into 4 discrete ranges. These arrays are used in a 3 step PCR procedure to rapidly identify the full length cDNA sequence for a DNA segment of interest. Thus, in one aspect of the present invention is based upon the use of arrays of preferably 5' enriched cDNA libraries as a means of high throughput full length cDNA cloning.

A. mRNA 5' Cap Structure Affinity Column Preparation

A problem with most cDNA libraries is that the bulk of the cDNAs present are not full length. This leads to the under-representation of mRNA 5' sequences in the sequenced clones and is inhibitory to future analyses. This problem is especially true for large transcripts which have been primed with oligo dT. Methods for the enrichment of cDNAs representing full length transcripts are known (I.Edery et al,. Molecular and Cellular Biology, 1995,15:3363–3371; P.Carninci, et al., Genomics, 1996, 37:327–336; CLON-TECHniques Technical Bulletin, 1996, January pp.2–4; K. Maruyama and S. Sugano, Gene, 1994, 138:171–174; S. Kato et al., Gene, 1994, 150:243–250; B. Schwer et al., Cell, 1987, 50:163–169; D. Muhlrad et al., Genes and Development, 1994, 8:855–866). The most promising of these methodologies are those described by either Ederly et al., 1995 or Caminci et al., 1996. Though differing in their approach, these two methodologies provide enrichment of cDNAs containing the mRNA 5' end by selecting for the presence of th 5' terminal $m^7$GpppN cap structure.

The current invention may utilize, but not be limited to, an affinity chromatography procedure similar to that of Ederly, et al. 1995, for the enrichment of full length cDNAs. In this embodiment, affinity selection is performed using the human eIF-4E protein coupled to a solid support matrix. To generate the affinity column, the coding region for the human eIF-4E cDNA (W. Rychlick et al., 1992, PNAS 84:945–949) is fused in frame into the commercially available vector, pGEX2T (Pharmacia) using standard molecular biological techniques. The fusion construct is expressed in *E.coli* and the hybrid GST-eIF4E protein purified by glutathione affinity selection according to the manufacturers recommendation. Preferably, the hybrid protein then undergoes a second round of affinity purification over $m^7$GDP-agarose as described by I. Edery et. al., Gene, 1988, 74:517–525. Following this second round of purification, the hybrid eIF-4E protein is rebound to the glutathione matrix to generate the cap protein affinity column.

B. Preparation of cDNA Libraries

In one example, four cDNA libraries from different tissue sources are prepared, each library comprising size fractionated cDNAs preferably enriched for full length mRNA sequences. Tissues used in this preparation are those known to contain complex mRNA species, e.g., brain, testes, placenta, and whole embryo. To construct these libraries, total and polyA$^+$ RNA is extracted from the selected tissues using standard procedures for molecular biology such as those disclosed by Sambrook et al., *MOLECULAR CLONING, A LABORATORY MANUAL*, 2nd Ed.; Cold Spring Harbor Laboratory Press, Cold Spring Harbor, N.Y., 1989. The polyA$^+$ RNA is then used to generate a cDNA library enriched for clones containing the authentic 5' mRNA end in accordance with procedures analagous to those described by I. Edery et al,. Molecular and Cellular Biology, 1995,15:3363–3371.

For example, in one embodiment, first strand cDNA is synthesized in reverse transcription reactions with Superscript II (Life Technologies) at 42° C. in the presence of methyl mercuric hydroxide (G. Frankel and A. Friedman, 1987, J Virol. Meth.18:1–12). Following first strand cDNA synthesis, duplexes consisting of full length or incomplete cDNAs are treated with the single-stranded nuclease, RNase A. This allows the removal of 5' methylated cap structures from incomplete cDNAs by degrading the RNA moity from less than full length RNA-cDNA hybrids. Full length cDNAs are then purified via their retained 5' cap structure by affinity selection using the human cap binding protein, eIF-4E, as described by Edery et al., 1995. Following CAP selection, the 5' enriched cDNAs undergo size selection using either standard chromatograpraphic or sucrose gradient technologies. For example, 5' enriched cDNAs are pooled into the following discrete size ranges: 1) 6.0 kb and above, 2) 3.0 kb to 6.0 kb, 3) 1.5 to 3.0 kb, and 0.6 to 1.5 kb. Following size fractionation, the cDNA pools are ligated into the appropriated plasmid vector, electroporated into *E.coli* and stored (sub-libraries made). (See FIG. 1)

It should be obvious to those skilled in the art that the 5° CAP selection is not required for the ultimate success of the present invention.

C. Preparation of cDNA Arrays and cDNA Pools

Most cDNA library screening protocols yield cDNA clones that may be incomplete. For example, database searches for related members of a specific gene family often yield short expressed sequence tags (ESTs) or incomplete EST assemblies. Standard approaches generally use the incomplete EST or assembly sequence information to generate hybridization probes for use against a cDNA library believed to possess the full length cDNA sequence. Unfortunately, such an approach often yields cDNA clones which are incomplete. Hence, there is a widespread need for a rapid and efficient method which permits the identification and selection of full length cDNAs from a library.

Several strategies for matrix pooling and the systematic screening of genomic libraries by PCR have been described (e.g., T. J. Kwiatkowski, 1990, Nuc. Acid Res. 18:7179–7192; E. D. Green and M. V. Olsen, 1990, Proc. Natl. Acad. Sci USA 87:1213–1217; C. T. Amemiya, 1992, Nuc. Acid Res. 20:2559–2563). Described here is an example of such a strategy which allows the rapid screening of over I million clones from a given cDNA library. To those familiar in the art, it will become apparent that the described strategy not only provides a simple method for arraying and pooling said library, but will also permits the rapid identification of long cDNA clones which contain the target sequence of interest. It should be noted that the example given below is intended as only one illustration of the general invention described in this application. Further variations are readily apparent to those skilled in the art.

An aliquot from each of the 4 size fractionated cDNA pools from a 5° CAP enriched library is titrated under the apropriate antibiotic conditions. Clones from a specific size fractionation pool are aliquoted into each well of a 96 well microtiter plate such that a total of 30 clones are present per well. Each microtiter plate contains a total of 2,880 clones derived solely from one size fractionation pool. A total of 384 96 well microtiter plates are prepared using aliquots from each of the size fractionation pools. Thus, a total of $1.106 \times 10^6$ colonies are arrayed for screening for each tissue library.

For each library, the arrayed microtiter plates are placed at 30° C. and the clones allowed to grow to an optical density of 0.1–0.7. Four replicas of each plate are then inoculated and grown as described above. The original microtiter plate set and two of the replica plate sets are stored by adding glycerol to 15% and freezing at –80° C. The remaining two replica plate sets are used to generate cDNA pools for screening.

96 Well Plate Row and Column cDNA Pools.

For each 96 well microtiter plate from one replica set, half of the culture from each well is combined into 8 pools corresponding to the 8 rows of the microtiter plate. The remaining half of each culture is combined into 12 pools corresponding to the 12 columns of the microtiter plate. This results in a total of 20 row and column pools for each of the 384 microtiter plates (7,680 pools total). Pools are stored by adding glycerol to 15% and placing at –80° C.

384 Well Plate Row and Column cDNA Pools.

Figure 2:
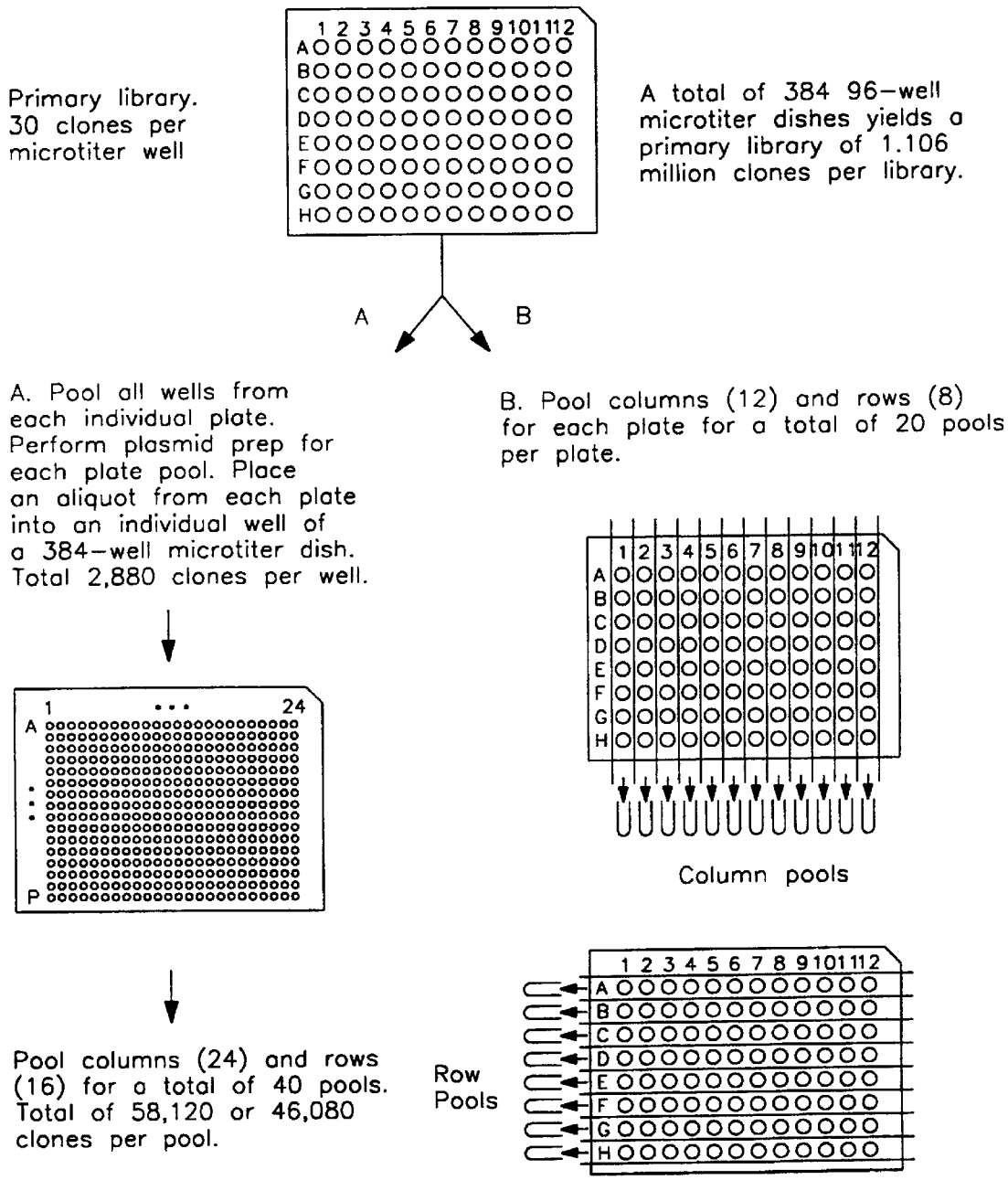
FIG. 2 Schematically describes one example of arraying and pooling clones from one tissue source into various microtiter plates.

The final replica plate set is used to generate single plate pools and row and column pools of purified DNA. To accomplish this, all of the cells from an individual plate are combined and the DNA purified for a total of 384 single plate pools. These single plate DNA pools are arrayed into the wells of a 384 well microtiter dish such that cDNAs derived from the same size fractionation pool are located in the the same region or quadrant of the plate. Equal aliquots from each of the 384 wells are combined into 16 pools corresponding to the 16 rows of the microtiter dish. Additionally, equal aliquots from each of the wells is combined into 24 pools corresponding to the 24 columns of the microtiter plate. This results in a total of 40 row and column pools for each independent tissue cDNA library arrayed. For the screening of 4 independent tissue cDNA librarys, a total of 160 pools are generated. (See FIG. 2)

The described row and column pools can now be screened by PCR. Alternatively, these pools can be spotted onto a solid support matrix for screening by hybridization. Such attachment and analysis of clones to a solid support is described in U.S. application Ser. No. 60/032,555 filed Dec. 12, 1996, which is incorporated by reference in its entirety.

Advantages of the current invention include a) the rapid, simultaneous screening of a large number of clones from 4 distinct cDNA libraries, b) the requirement of knowing only a short amount of sequence information for each DNA sequence of interest, and c) the ability to reject shorter, incomplete cDNA clones from the analysis.

A. PCR Screening

In one embodiment for full length cDNA clone identification, PCR primer pairs are designed from the partial cDNA of interest. Preferably PCR primers are pretested for suitablility in a background of library mixture diluted to approximately 1/100,000 clones. PCR is then performed against the 40 row and column pools of purified DNA derived from the 384 well microtiter dish. A total of 160 PCR reactions are performed to screen 4 entire different tissue libraries. Sizes of the reaction products are measured by gel electrophoresis to identify row and column pool(s) generating the appropriate PCR product. Row and column identification permits the identification of both the original insert size fraction pool and the original 96 well microtiter plate containing the clone of interest. PCR is then performed on the 20 row and column culture pools derived from the positively identified 96 well microtiter plate(s) having the largest cDNA insert size. Gel electrophoresis is once again used to determine the row and column pools which generate the appropriately sized PCR product and thereby identify the specific microtiter well(s) possessing the desired full length cDNA clone. An aliquot from the identified wel(s) is plated onto selective media and allowed to grow overnight. 96 colonies are then picked and undergo PCR analysis. PCR products are analyzed by gel electrophoresis and the positive clones identified. In a preferred embodiment, clones derived from separate cDNA libraries are submitted for further analysis.

B. Sequence Verification

DNA from colonies positive by PCR analysis is prepared and sequenced using standard methodologies. Clone verification is determined using standard computational programs.

C. Other Methods of the Invention

As is obvious to one skilled in the art upon reading this disclosure, the compositions and methods of the invention can be used for other similar purposes. For example, the clone array and pooling format employed in the above embodiment was chosen for both clarity and ability to generate sans robotics. However, another embodiment is to robotically pick independent, size selected clones into individual wells of microtiter dishes. These individual clones are then pooled into the above described matrix for three rounds of PCR screening. A potential advantage of this embodiment is that clones are grown in individual wells and therefore potentially more equally represented in the final poolings. Another alternative is to choose PCR primer pairs such that one primer is complementary to the 5' end of the cDNA insert and the other to the library vector. In this embodiment, the size of the product indicates which pool contains the longest positive cDNA clone.

As is obvious to those skilled in the art, it is not always possible to generate a specific PCR product using complex templates (pools). For these cases, PCR is used against the original, truncated cDNA clone to generate hybridization probes for use against cDNA arrays or high density grids. Such cDNA arrays can be generated using any of the compositions of the present invention, e.g. the original 96 well plates containing 30 clones per well, the 20 row and column pools derived from each of the 96 well plates, the purified DNA plate pools derived from the 96 well plates, the 40 row and column purified DNA pools derived from the arrayed 384 micrototer well plate. (Alternatively, one could grid the original size selected cDNA library as individual clones.)

What is claimed is:

1. A method for high throughput full length cDNA cloning comprising:

(a) preparing cDNAs from mRNAs;

(b) size selecting the cDNAs into discrete n ranges;

(c) transforming host cells with cDNAs from the each discrete n size ranges to make n separate sub-libraries;

(d) placing up to m number of clones from each n sub-libraries into individual wells of k numbers of microtiter plates, each microtiter plates containing x numbers of rows and y numbers of columns, in a fashion that clones from each n sub-library will go into n separate sets of microtiter plates within the total k number of microtiter plates;

(e) pooling all the clones from individual microtiter plates, and placing each pool of clones into wells of a second separate microtiter plate containing i rows and j columns, the second microtiter plate containing a total of k number of wells in such a fashion that placement of pools of clones will be placed in separate n regions within the microtiter plate in order to facilitate the identification of cDNA insert sizes;

(f) identifying the well location of cDNA of interest in the second microtiter plate which has the longest insert; and correlating the well located to one of the earlier k number of microtiter plates; and (g) identifying the well location in the microtiter correlated in step (f) for the cDNA of interest; and in which m is a positive integer equal or greater than one; n, k, x, y, i, and j are positive integers greater than one; with the proviso i times j equals k.

2. The method of claim 1 which further comprises the step of enriching the cDNA which are full length after step (a) but before step (b).

3. The method of enriching for the full-length cDNA of claim 2 comprising treating cDNA/mRNA duplexes with the single-stranded nuclease, RNase A, and purifying full-length cDNAs via their retained 5° CAP structure by affinity selection using the human cap binding protein, eIF-4E.

4. The method of claim 3 which further comprises the step of picking the clone with cDNA of interest if the well identified in step (g) contains more than one clone (i.e. m greater than 1).

5. The method of claim 1 in which steps (f) and/or (g) comprise performing PCR reaction with primers derived from cDNA of interest with pooled product of rows and columns.

6. The method of claim 1 in which steps (f) and/or (g) comprise performing hybridization reaction with cDNA of interest with pools spotted on a solid matrix support.

7. The method of claim 2 in which steps (f) and/or (g) comprise performing PCR reaction with primers derived from cDNA of interest with pooled product of rows and columns.

8. The method of claim 2 in which steps (f) and/or (g) comprise performing hybridization reaction with cDNA of interest with pools spotted on a solid matrix support.

9. The method of claim 3 in which steps (f) and/or (g) comprise performing PCR reaction with primers derived from cDNA of interest with pooled product of rows and columns.

10. The method of claim 3 in which steps (f) and/or (g) comprise performing hybridization reaction with cDNA of interest with pools spotted on a solid matrix support.

11. The method of claim 4 in which steps (f) and/or (g) comprise performing PCR reaction with primers derived from cDNA of interest with pooled product of rows and columns.

12. The method of claim 4 in which steps (f) and/or (g) comprise performing hybridization reaction with cDNA of interest with pools spotted on a solid matrix support.

13. The method of claim 1, 2, 3, 4, 7, 8, 7, 8, 9, 10, 11, or 12 in which n is 4, m is 30; k is 384; x is 8; y is 12; i is 16; and j is 24.

\* \* \* \* \*